United States Patent [19]
Fell et al.

[11] Patent Number: 4,889,524
[45] Date of Patent: Dec. 26, 1989

[54] PORTABLE CENTRIFUGE APPARATUS

[75] Inventors: Claude Fell, Nyon, Switzerland; Etienne Pagés, Divonne, France; Dominique Uhlmann, Nyon, Switzerland

[73] Assignee: Haemonetics Corporation, Braintree, Mass.

[21] Appl. No.: 93,366

[22] Filed: Sep. 4, 1987

[51] Int. Cl.$^4$ ............... B04B 7/06; B04B 9/12
[52] U.S. Cl. .................................. 494/12; 494/60
[58] Field of Search ............. 494/12, 41, 43, 45, 494/60, 63, 77, 81, 82, 83, 84; 604/5, 6

[56] References Cited

U.S. PATENT DOCUMENTS

| | | | |
|---|---|---|---|
| 2,019,827 | 11/1935 | Odajima | 494/60 X |
| 3,317,127 | 5/1967 | Cole | 494/43 |
| 3,581,981 | 6/1971 | Latham . | |
| 3,706,412 | 12/1972 | Latham . | |
| 3,785,549 | 1/1974 | Latham . | |
| 3,970,245 | 7/1976 | Aeschlimann | 233/24 |
| 4,010,893 | 3/1977 | Smith et al. | 494/12 X |
| 4,086,924 | 5/1978 | Latham . | |
| 4,140,268 | 2/1979 | Lacour | 233/1 A |
| 4,303,193 | 12/1981 | Latham . | |
| 4,341,342 | 7/1982 | Hara | 494/60 X |
| 4,412,831 | 11/1983 | Avery et al. . | |
| 4,498,532 | 3/1985 | Harbott | 494/43 X |
| 4,530,691 | 7/1985 | Brown | 494/45 |
| 4,636,193 | 1/1987 | Cullis | 494/45 |
| 4,639,242 | 1/1987 | Babson | 494/37 |

FOREIGN PATENT DOCUMENTS

0257755A1 2/1988 European Pat. Off. .
2181371A 4/1987 United Kingdom .

Primary Examiner—Harvey C. Hornsby
Assistant Examiner—Scott J. Haugland
Attorney, Agent, or Firm—Hamilton, Brook, Smith & Reynolds

[57] ABSTRACT

A portable centrifuge apparatus for use with a centrifuge bowl having a seamless, unitary blow molded bowl body for the separation of blood into less dense and more dense components. A light weight, hand-held cabinet houses the centrifuge, and auxiliary equipment such as blood pumps, control instrumentation, and a sensor for measuring fluid pressure in a disposable chamber used for filtering blood.

18 Claims, 11 Drawing Sheets

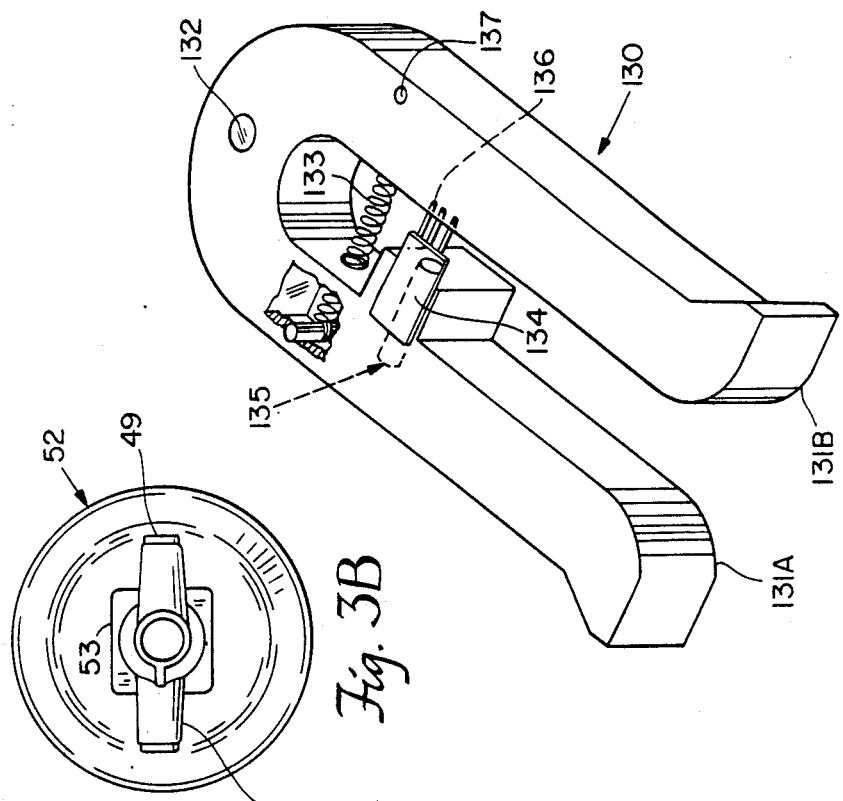
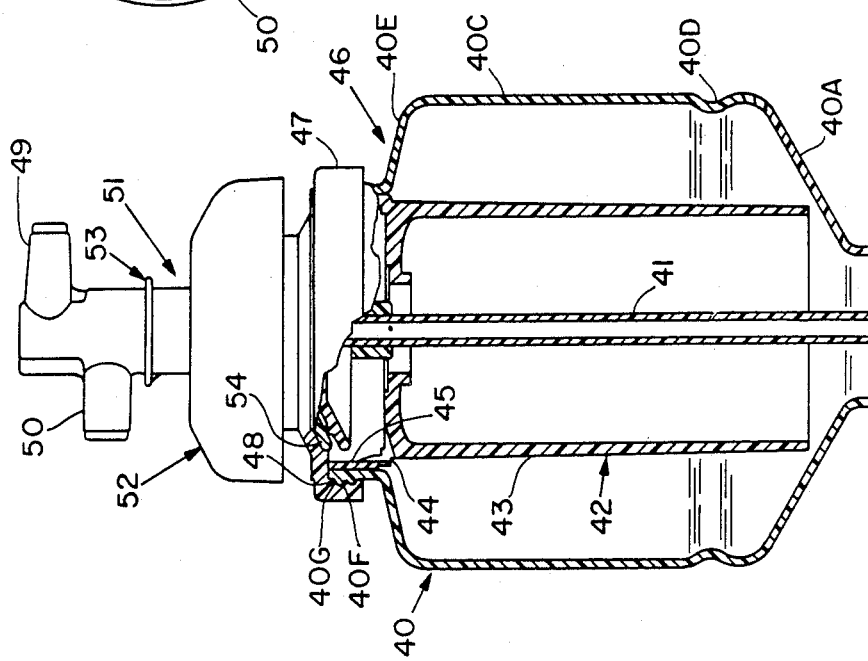

PORTABLE CENTRIFUGE APPARATUS

BACKGROUND OF THE INVENTION

The invention relates generally to apparatus for separating blood or other biological fluids into their constituent components, such as in plasmapheresis or cell washing. Centrifuges have been developed for the purpose of rapidly, efficiently, and inexpensively effecting this separation in a sterile environment.

It should be noted that while the present system will be described in connection with a plasmapheresis application involving separation of anticoagulated whole blood, other biological fluids and other applications, such as the above-mentioned cell washing process, are contemplated.

A plasmapheresis process is described in U.S. Pat. No. 4,086,924, wherein blood withdrawn from a donor is mixed with an anticoagulant, transported to a rotatable plasmapheresis centrifuge bowl and mounted on a chuck for separation into plasma and non-plasma components. The centrifuge bowl generally comprises a multipiece feed tube and seal assembly with a central input port which introduces whole blood through a longitudinal feed tube into the bottom of the bowl. A central output port is provided to allow the separated plasma to flow out of the bowl. The '924 patent also discloses the use of a standard pressure transducer to monitor fluid pressure in the system.

These bowls disclosed in the prior art have one or more seams in the bowl where the bowl parts have been welded together. These bowls are not well balanced about the rotational axis and require the use of adaptors for fitting the bowl into the chuck for rotation by a motor. The adaptors are normally lined with an elastomeric material for gripping the bowl.

Existing centrifuges for blood processing are typically bulky and too heavy for hand-carried, portable use. Systems typically weigh between 80 and 300 pounds and are transported on platforms with rollers. U.S. Pat. No. 4,412,831, for example, discloses a centrifuge apparatus transported on rollers. A belt driven gear is used to drive the centrifuge bowl. A flexible bearing mount system is used to ensure alignment of the axis of rotation of the rotor with the changing direction of the rotor's angular momentum vector.

In the pending application, U.S. Ser. No. 888,764, filed on July 22, 1986, "PLASMAPHERESIS CENTRIFUGE BOWL" wherein a seamless one-piece bowl body with a rotary seal and header assembly is described. Due to the blow molding process, the balancing of the bowl is maintained within very tight tolerances.

SUMMARY OF THE INVENTION

The present invention comprises a portable centrifuge unit having a light-weight assembly for holding and rotating a disposable, seamless, unitary bowl for plasma separation.

The bowl is held in a chuck rotated by a motor without the use of adaptors or balancing sleeves. The housing for the centrifuge has a closeable cover with a sensor for indicating that the cover is closed. A lock for securing the cover and means for detecting whether the lock is engaged is also provided.

The centrifuge system has a hollow longitudinal axis permitting the expelling of air displaced by insertion of the bowl into the chuck. The hollow axis also permits easy cleaning of the centrifuge system.

The centrifuge system is housed in a portable, lightweight, cabinet made of polyester reinforced fiber. The inside bottom of the cabinet has projecting molded platforms for supporting the centrifuge and other heavy instrumentation. Panels on the left and right side are provided with handles for easy transport of the system. The cover folds open with the inside of the cover housing a display and a control switch panel. The cover is inclined at about 30° to permit ease of viewing. With the cover open there is also direct access to the centrifuge, pumps, and control sensors. When the cover is closed it operates to protect components during transport of the unit. A bar handle rotates up over the closed cover to permit carrying by hand. The front panel is provided with an aperture through which a monitor for measuring the flow of blood from a donor is accessed.

A device for measuring blood pressure in the stream passing through the centrifuge system employs a Hall effect sensor to measure the variation in distance between two displaceable arms which engage the exterior walls of the conduit carrying the flow of blood. A magnet mounted on one arm generates a magnetic field across a Hall effect sensor mounted on the second arm. The position of the sensor with respect to the field changes as the distance between the two arms fluctuates. This variation in the distance between the two arms generates an electrical signal which is calibrated and used to indicate the fluid pressure within the conduit.

The above and other features of the invention, including various novel details of construction and combinations of parts, will now be more particularly described with reference to the accompanying drawings and pointed out in the claims. It will be understood that the particular plasmapheresis centrifuge embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 3A is a partial cross-sectional side view of centrifuge bowl and head assembly.

FIG. 3B is a top view of the head assembly of FIG. 3A illustrating the molded panel for holding the head stationary.

FIG. 9 is a perspective view of a pressure monitor employing a Hall effect sensor for monitoring fluid pressure in a conduit.

DETAILED DESCRIPTION OF THE INVENTION

Figure 1:
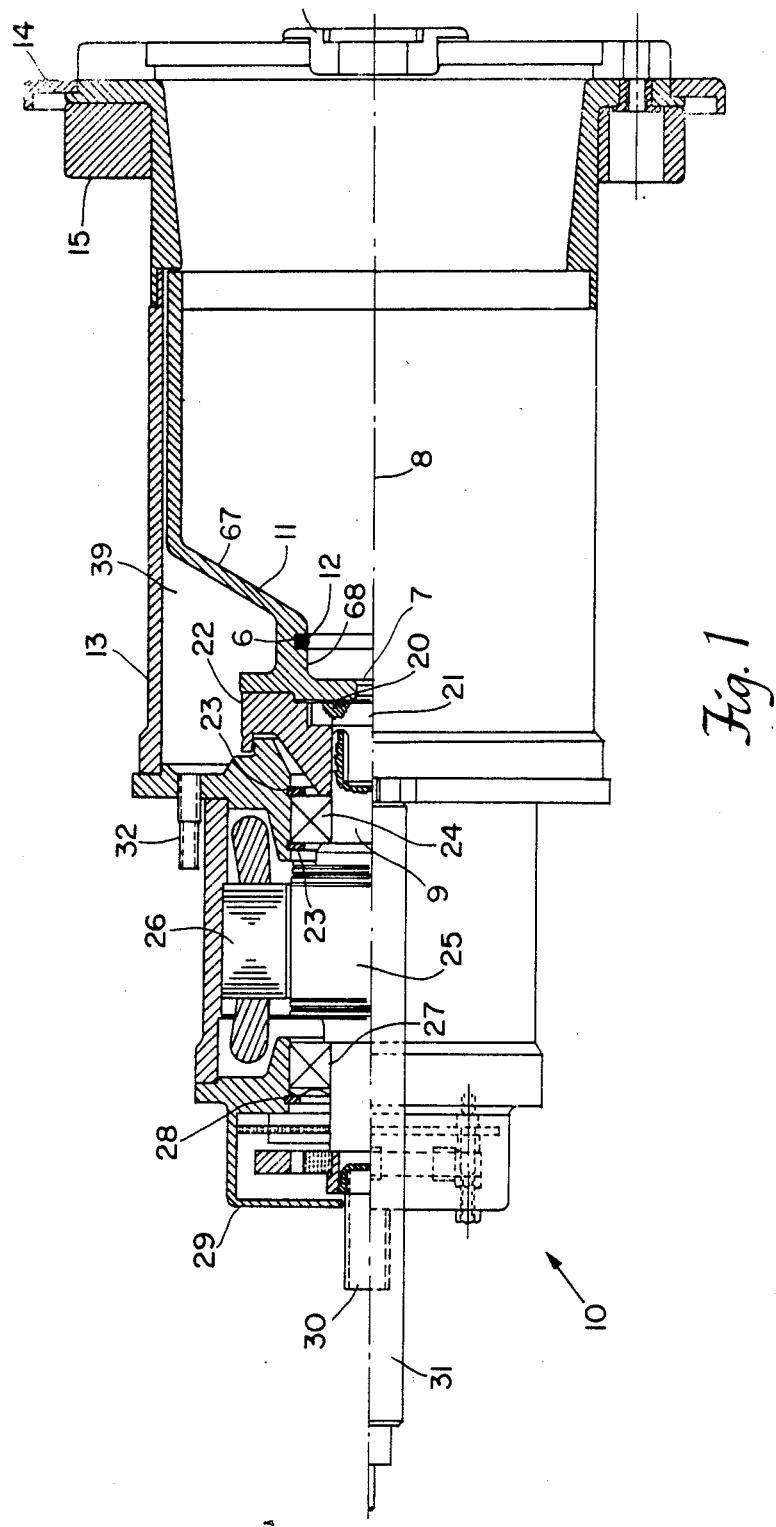
FIG. 1 is a partial cross-sectional cut-a-way view of the centrifuge rotor and chuck assembly.

The centrifuge apparatus 10 for the ultra-light plasmapheresis system is illustrated in FIG. 1. It should be noted that the apparatus of FIG. 1 is intended to operate when mounted vertically with feet 31 at the bottom and holder 18 at the top. A chuck 11 of generally cylindrical shape with a lower inclining wall portion 67 and vertically inclined end wall portion 68 and a longitudinal axis corresponding with the longitudinal axis 8 of the centrifuge is housed within a cylindrical stationary bucket 13. The chuck 11 is used to cradle the seamless fluid containing centrifuge bowl described in FIG. 3.

The chuck 11 has an O-ring 12 mounted in groove 6 on the inside of end wall portion 68. The O-ring frictionally engages the lower outer surface of an inserted centrifuge bow (not shown) so that the chuck and bowl will rotationally accelerate together without slippage. In a preferred embodiment groove 6 conforms to the outward shape of the bowl at the area of engagement. The chuck 11 is mounted onto an adaptor 22 with screws (not shown). The adaptor is then rigidly attached to the shaft 9 by retaining nut 21. There are two bearings 24, 27 to insure proper alignment of the shaft 9. One of these bearings 24 is disposed adjacent the adaptor 22. The bearings are held in place by circlips 23,28. A second O-ring 20 is placed between the nut 21 and the chuck 11 to prevent any fluid collecting in the chamber 39 between the outer bucket 13 and the chuck 11 from entering into the motor assembly. An outlet port 32 is provided to drain any fluid collecting in the chamber 39 between bucket 13 and chuck 11.

Shaft 9, threaded at one end to receive nut 21, is rigidly attached to the adaptor 22 and the rotor 25. The motor is comprised of stator 26 and rotor 25.

A tachometer assembly 29 has been placed adjacent the motor to monitor its rotational speed and provide an electrical feed-back signal to control the speed.

Figure 6:
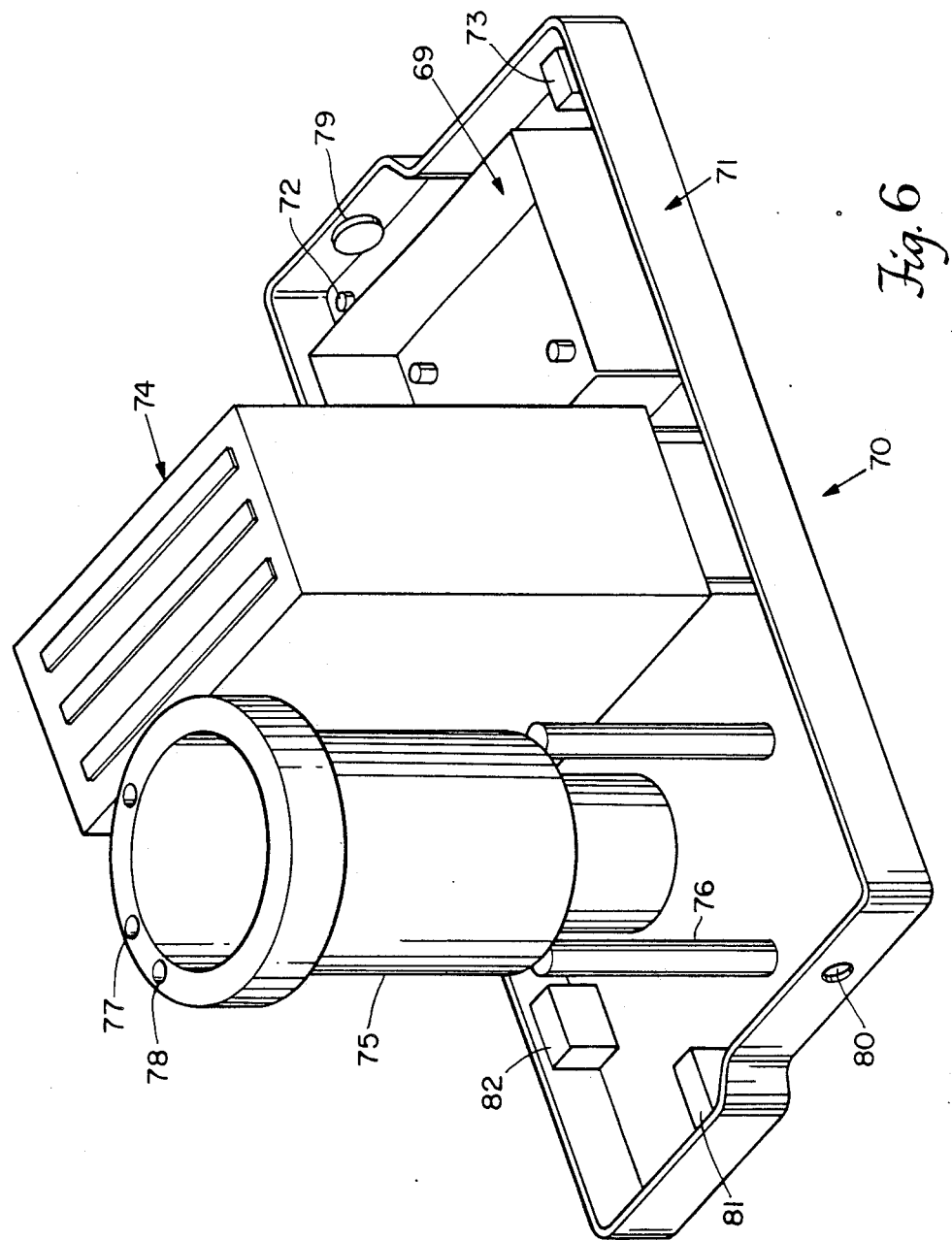
FIG. 6 illustrates in plan view the base panel used for supporting system components.
Figure 7:
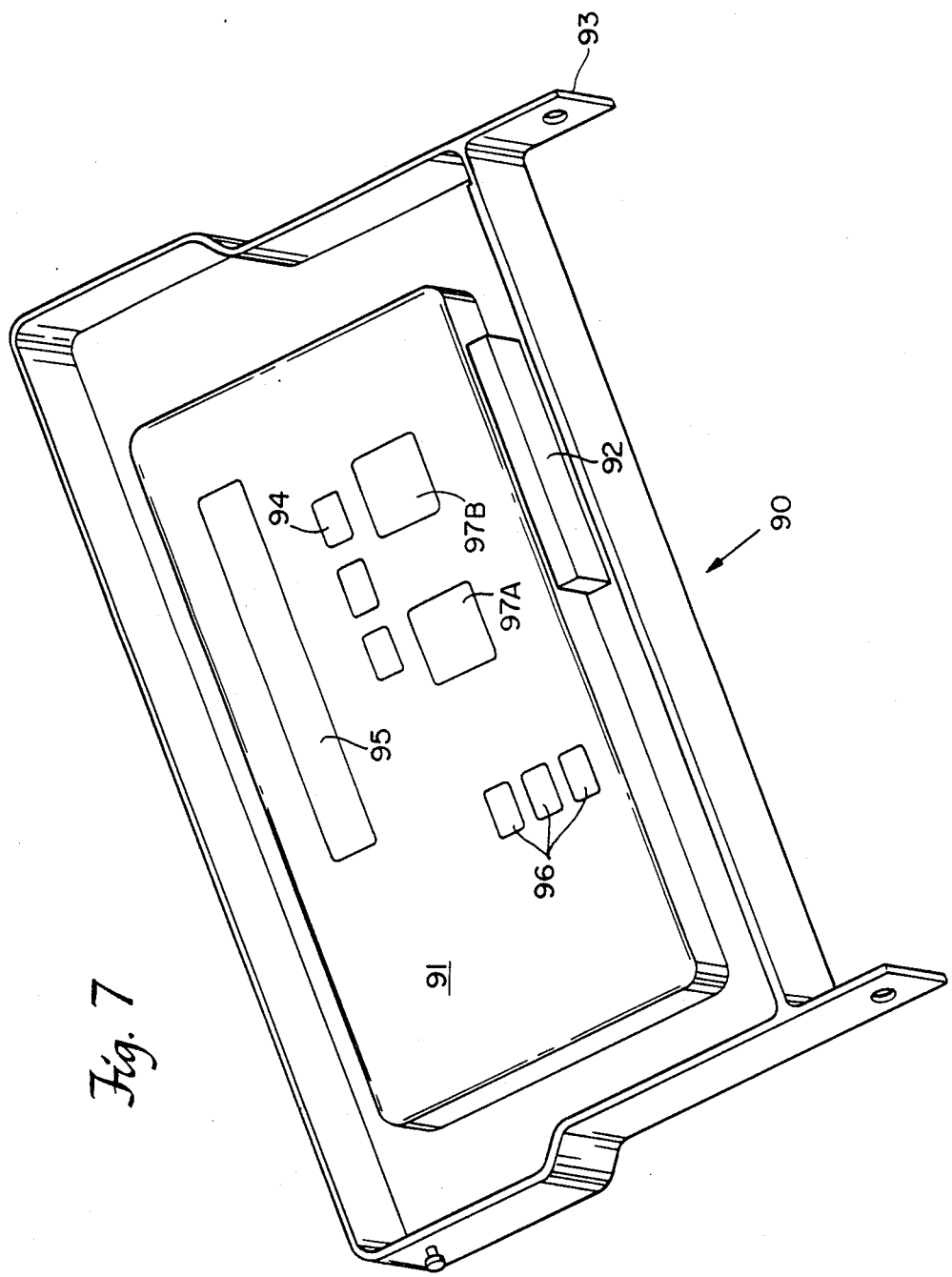
FIG. 7 illustrates the in plan view inside surface of the cover with a display panel mounted thereon.

Three cylindrical feet 31 are used to mount the centrifuge into the cabinet base which is further illustrated in FIG. 6.

Note that the longitudinal axis 8 of the centrifuge is hollow from the circular opening 7 in the base of the chuck 11, through the shaft 9, rotor 25, and tachometer assembly 29. This permits the interior to be easily cleaned and also allows air, caused by the insertion of the bowl into the conformably shaped chuck 11 to be expelled, thus permitting easy insertion of the bowl into the chuck.

A steel ring 15 is affixed to the upper rim of the centrifuge to damp out any excess vibration due to the bowl rotation. An outer rim 14 is used to shield or block any liquid from entering the cabinet from around the top of the centrifuge.

Figure 2:
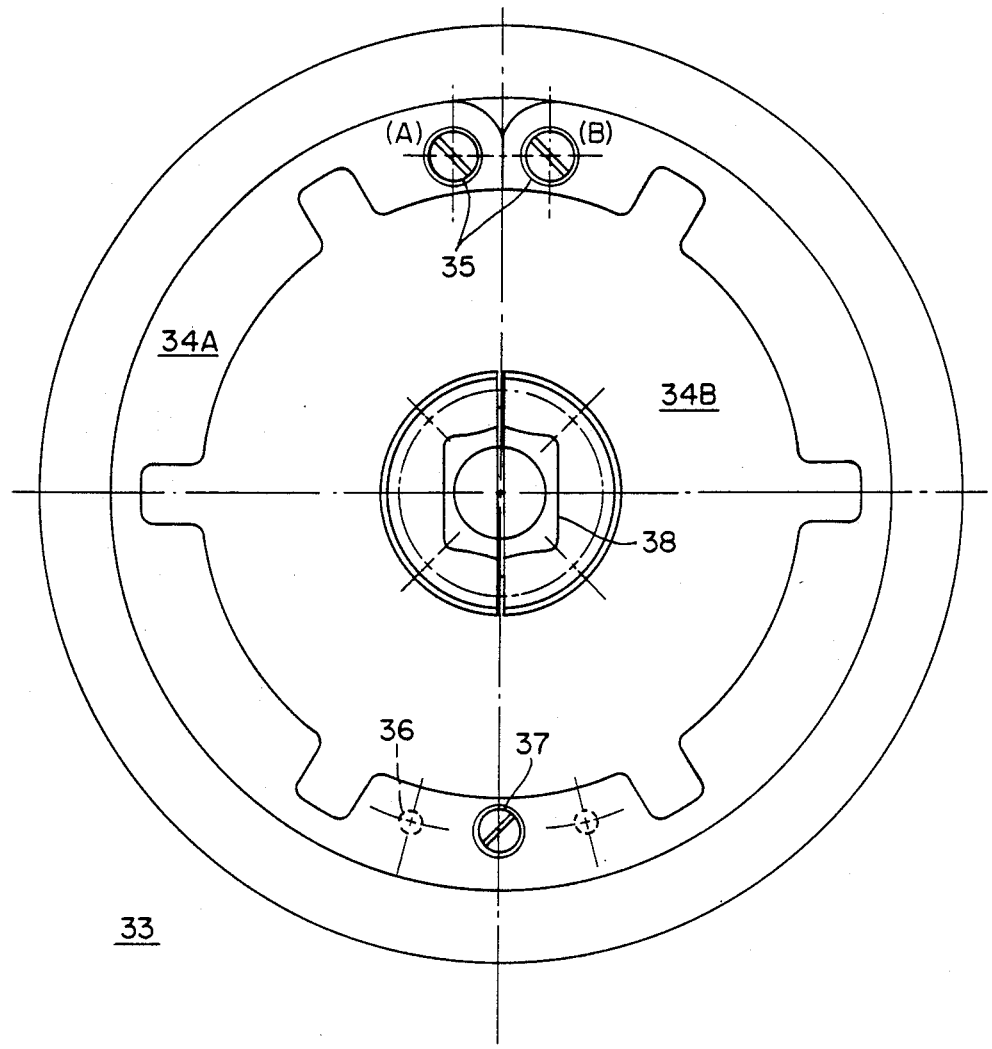
FIG. 2 is a top view of the centrifuge of FIG. 1 illustrating the cover apparatus.

A cover assembly 33, along with associated bowl head holder 18, lock 37 and safety switches 36 are illustrated in both FIGS. 1 and 2. The top view of FIG. 2 shows that the cover assembly 33 is comprised of two symmetric, planar, semi-circular and transparent half-discs 34A and 34B. Each half disc 34A and 34B, has a separate axis of rotation 35A and 35B, respectively. Each half disc rotates in the plane of FIG. 2, that is, in a plane orthogonal to centrifuge axis 8. The half-discs are rotated in opposite directions to assume an open position for inserting the centrifuge bowl. When closed, both half discs of the cover meet or abut at locking screw 37, which can be tightened by hand to lock the halves in place.

Two safety mechanisms have been incorporated into the cover apparatus to insure that both cover components are secure during operation. If one or both of the cover halves are not held in place, the bowl head holder 18 cannot maintain the bowl head 51 (FIG. 3) in a stationary position. This embodiment of the invention requires that the bowl head be stationary for the bowl and centrifuge to separate blood properly.

Each half of cover 33 has a Hall effect sensor 36 attached adjacent to the lock 37. A magnet (not shown) is positioned opposite each sensor when both covers are in the closed position. Each sensor sends an electrical signal to the control electronics of the system only when each cover is closed. Thus when one or both covers are open the motor is disabled by the main control program of the system.

Similarly, the lock screw 37 has a second safety mechanism where the lock must be in the "locked" position and send an electrical signal to the main control program before the system will operate.

The bowl head holder 18 has a square or rectangular molded inset 38. Each half cover 34A and 34B incorporates inset 38. Inset 38 engages and clamps a molded panel 53 (FIG. 3B) rigidly attached to the bowl head. The shape of the complete inset 38 conforms almost exactly with the shape of the molded panel 53 so that little or no relative movement is possible between the covers 34 and the bowl head during centrifuge operation.

The disposable bowl assembly of FIGS. 3A & B is comprised of two basic items: a rotary seal and header assembly 51; and a unitary, seamless, one-piece bowl body 46.

The seal and header assembly 51 has a feed tube 41 extending from transverse inlet port 49 to provide an inlet path for anticoagulated whole blood into the bottom portion 40B of bowl body 46. The shield 52 covers a rotary seal (not shown) and an axial bore which extends from the effluent tube 54 to the outlet port 50.

The header and seal assembly 51 is mated with bowl body 40 using threads 40F along the upper ring 40G of the bowl.

The bowl body 40 is an integral body adapted to be manufactured by blow molding or injection blow molding and may be formed of a suitable plastic. The bowl body is formed of an upper ring portion 40G, an upper diagonal portion 40E, a middle central portion 40C, a lower diagonal portion 40A, and a bottom cross portion 40B. A groove is formed about the periphery of the bowl at 40D to form a holding surface so that the bowl may be used with prior art centrifuge chucks using adaptors to hold the bowl. The present centrifuge apparatus could alternatively be mated with a bowl body having a smooth central portion 40C without the peripheral groove 40D, since only the bottom portion 40B of the bowl is frictionally engaged by the chuck.

An O-ring gasket 48 is disposed on an inner peripheral shoulder of crown member 47 adjacent threads 40F. When member 47 is threaded onto the bowl body 40, gasket 48 is compressed against the upper wall of ring 40G forming a liquid-tight seal.

A cylindrical walled core 42 is inserted through an opening in ring portion 40G and has a cylindrical outer wall 43 coaxial to the axis of the bowl body 46. An upper ring portion 45 of core 42 is adapted to abut the inner wall of ring portion 40G.

Blood separation within the bowl body 46 during centrifuge operation will now be described in general. Whole blood is coupled from inlet port 49 through the feed tube assembly 41 to the bottom of the spinning centrifuge bowl. The heavier red blood cells are forced radially outward from the central axis and are retained along the inner bowl wall of the central portion 40C of the bowl. The lighter, less dense plasma is captured on the outer surface of cylindrical wall 43 and allowed to exit through the slots 44 at the top of wall 43 whereupon they pass through the effluent channel 54 and out through the outlet port 50.

The cabinet used for housing the centrifuge and other system components is illustrated in FIGS. 4-8. The relatively low weight and size of the unit makes this design highly useful for portable applications.

Figure 4A:
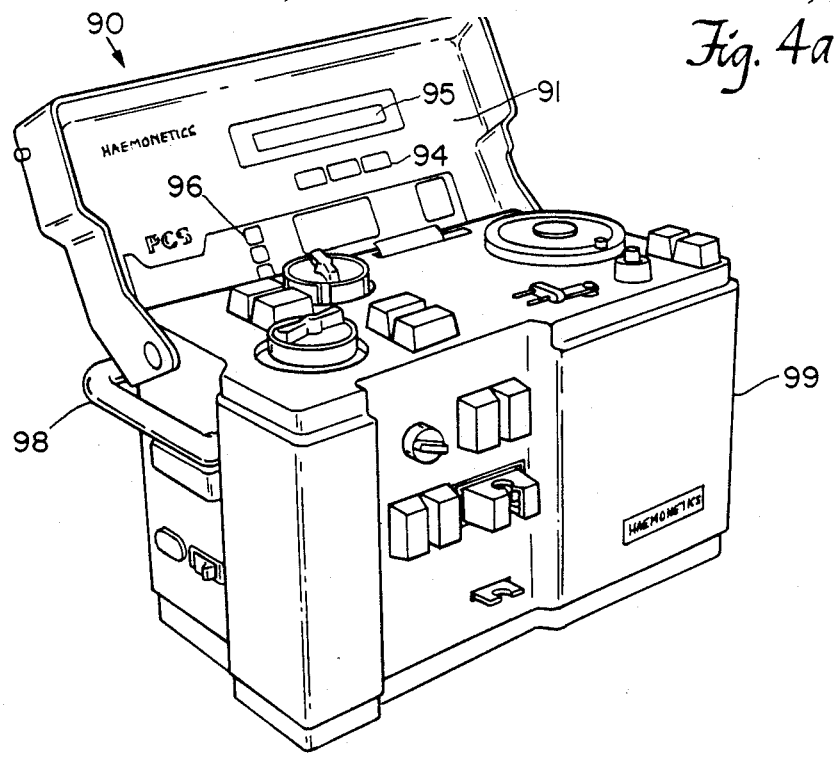
FIG. 4A and 4B illustrate, respectively, front and rear perspective views of the cabinet used for housing the centrifuge apparatus.
Figure 4B:
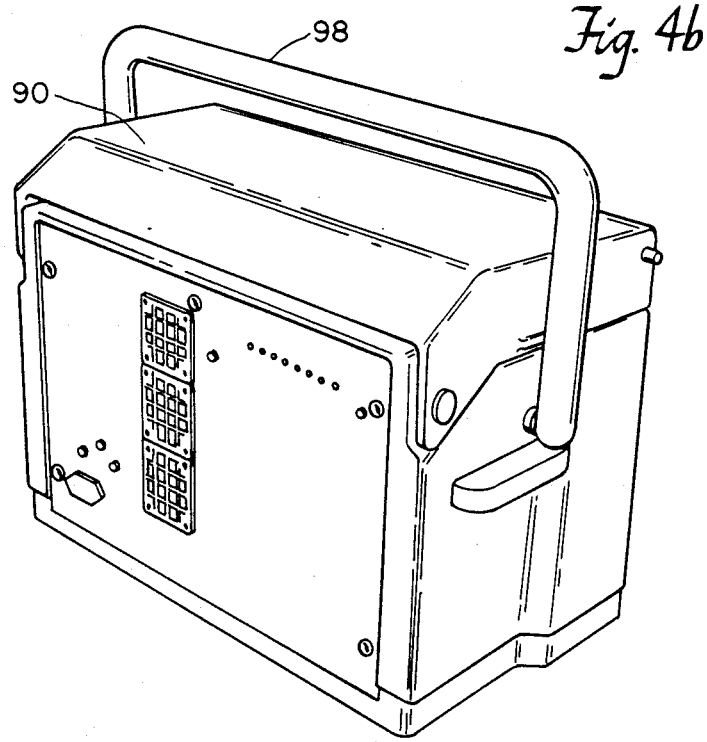

FIGS. 4A and 4B show perspective views of the system as a whole. The cover 90 provides access to operator controlled instrumentation. When the cover 90 is closed, a handle 98 rotates to a position above the cabinet for easy transport of the unit. When the cover 90 is open, as illustrated in FIG. 4A, it is inclined at an approximate 30° angle for ease of viewing. The cover 90 has a panel 91 (see FIG. 7) mounted on the inside of the cover with various display and control functions incorporated therein. A liquid crystal display 95 allows monitoring of warnings and control information by the operator. Membrane switches 94 allow direct control and programming by the operator of functions or modes of operation, such as Draw, Return, or Stop. Switches 96 control the pump speed and allow it to be varied. Control 97A allows the modification of programmed parameters; and 97B allows selected parameters to be permanently stored. A connector 92 provides power to panel 91 through the central portion of the unit.

The base 70 illustrated in FIG. 6 provides support for the installation of the heavier components. The centrifuge 75 and card cage 74 are supported by legs 76 affixed to the base 70. The main power supply 69 receives power from a standard voltage source through plug 73 and directs power to various system elements including the centrifuge motor 26, the cover display 95, and a pressure sensor mounted in the base with access through the front panel 99 of the cabinet. The card cage 74 contains a central microprocessing unit which performs various programmed functions. A speaker 79 provides an audible alarm in case of system malfunction. A pressure cuff 65 shown in FIG. 12 about the arm of the donor is pneumatically connected to a compressor 81 through connector access hole 80. A cuff pressure monitor 82 provides feed-back to the control program 64.

Figure 8:
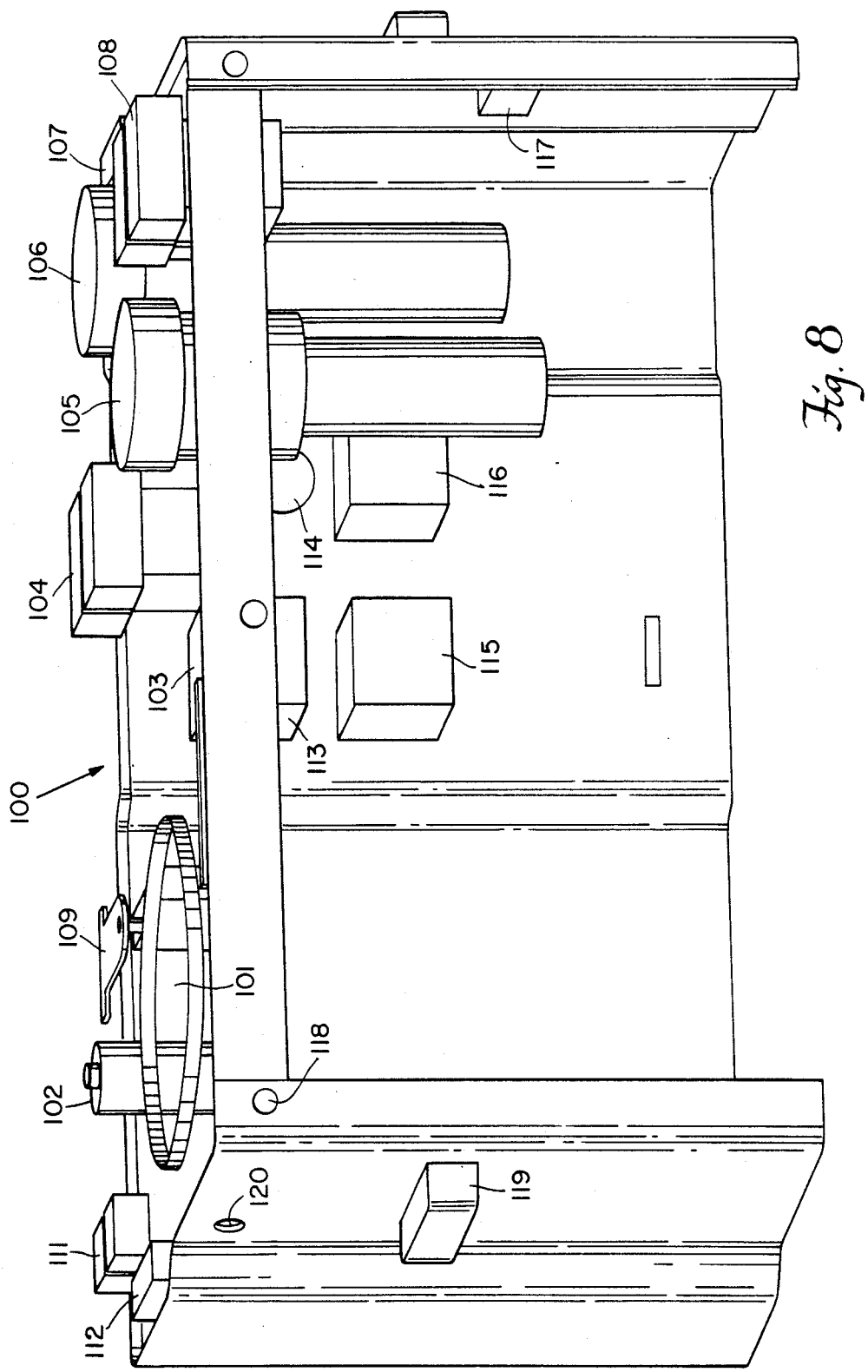
FIG. 8 illustrates in plan view the central portion supported by the front, left, and right side panels.

FIG. 8 illustrates the central portion and sides of the apparatus along with many of the functional elements. Blood is withdrawn from a patient where the flow rate and fluid pressure are measured while the whole blood is transported through tubing to a blood pump 106, and hence into the bowl 40 for centrifuging. There are three air detectors, one primary 104, and first 113 and second 116 backup detectors. These are used to ensure that the blood plasma is free of air before centrifuging and that blood components returned to the donor after centrifuging are also free of air.

Donor lights 107 and 112 indicate to the donor the status of his blood flow. Optical line sensor 111 provides for the detection of red blood cells in the line after centrifuging. Clamp 102 is used to pinch the tubing when the centrifuge is braking to avoid contamination of the plasma by red blood cells.

Figure 12:
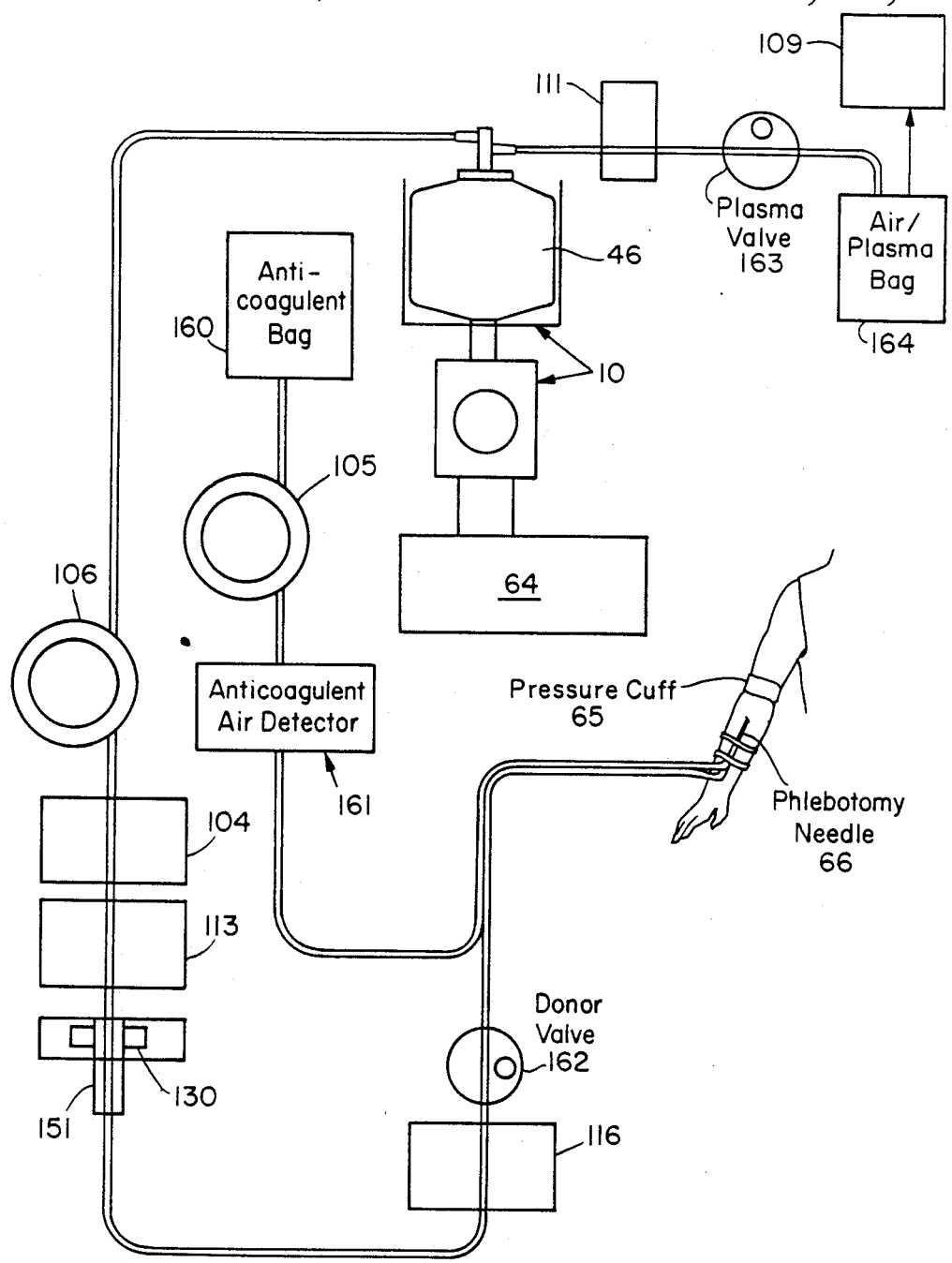
FIG. 12 illustrates, in schematic form, a plan view of the blood flow through the system components.

There is also an air detector 161 in the path of the anticoagulant as shown in FIG. 12 along with anticoagulant bag 160. This anticoagulant is mixed with blood withdrawn through needle 66.

The central portion 100 is connected to front 99 and side panels 121 and 122 in FIG. 8. Each side panel is fitted with handles 119, and holes 120 for receiving the main handle which rotates about the axis through the holes. The front panel has apertures for providing operator access to the various monitoring components described above.

Figure 5:
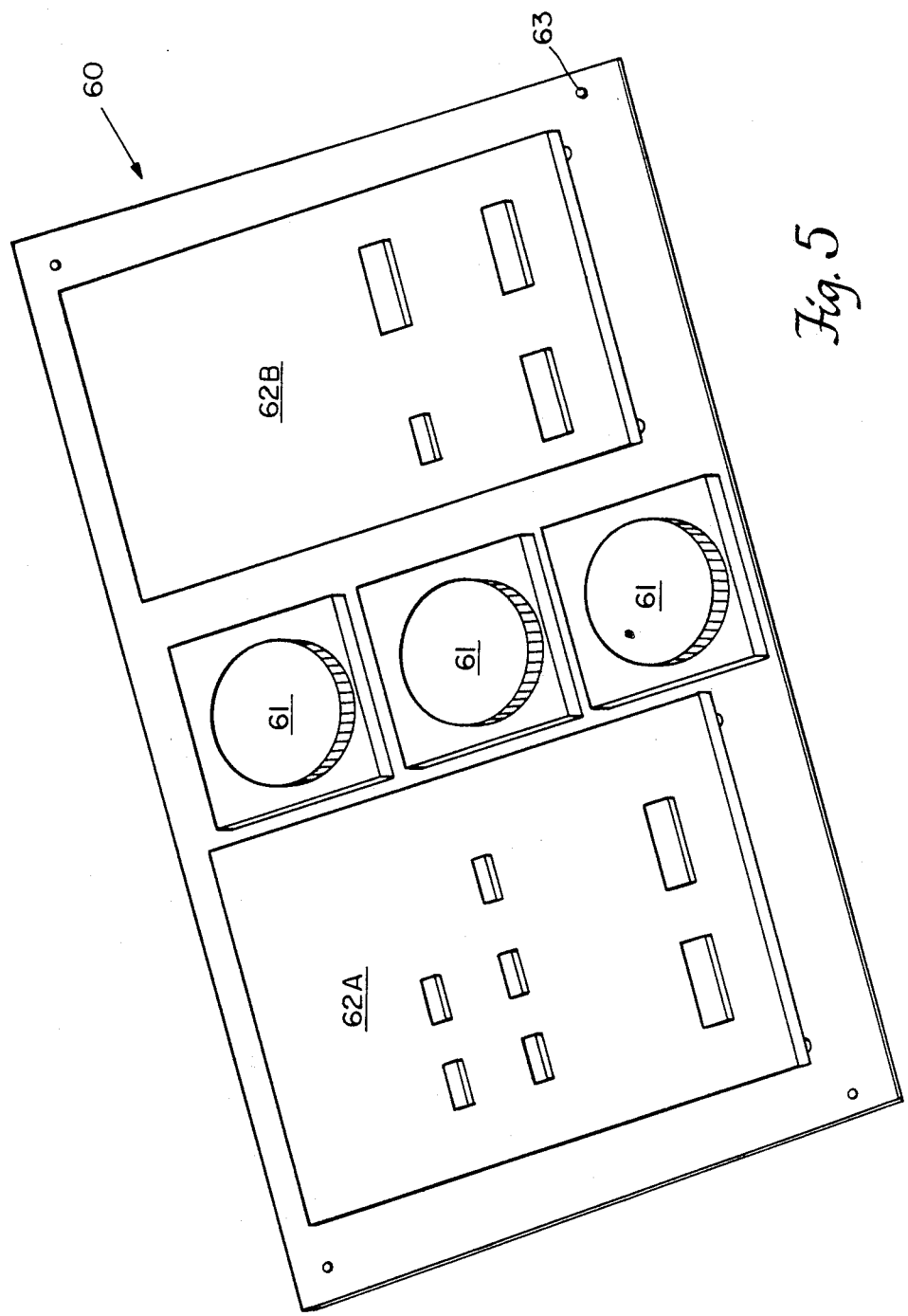
FIG. 5 illustrates in plan view the back panel with system components of a preferred embodiment mounted thereon.

The back panel, illustrated in FIG. 5, has cooling fans 61 mounted in the center. Printed circuit boards 62A and 62B are mounted on each side of the array of fans 61. 62B houses the driver electronics of the centrifuge. 62A houses the driver electronics of the pumps 105 and 106 and the plasma and donor valves shown in FIG. 12.

Figure 10:
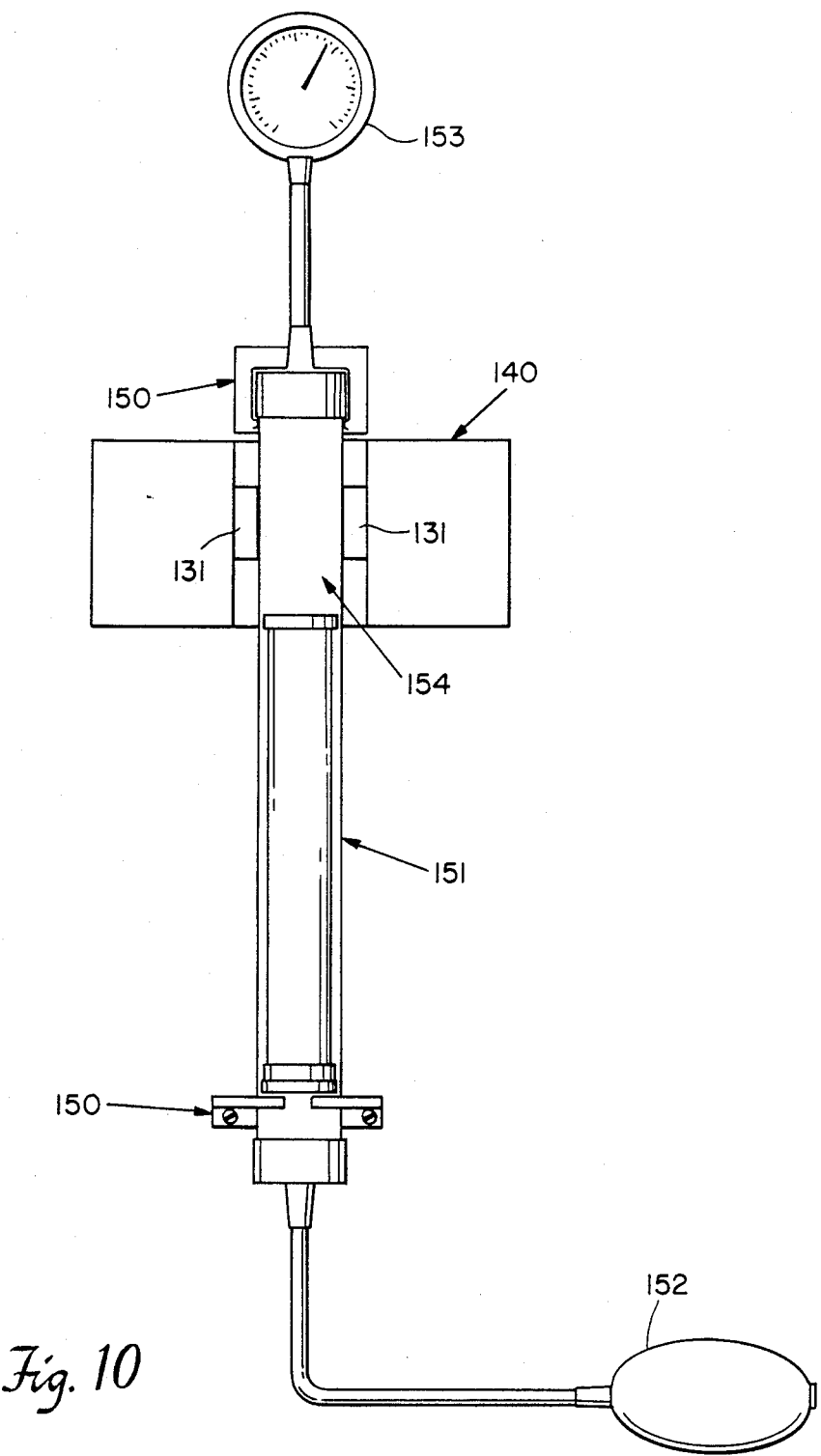
FIG. 10 schematically illustrates a calibration system for the pressure sensor and filter chamber.
Figure 11:
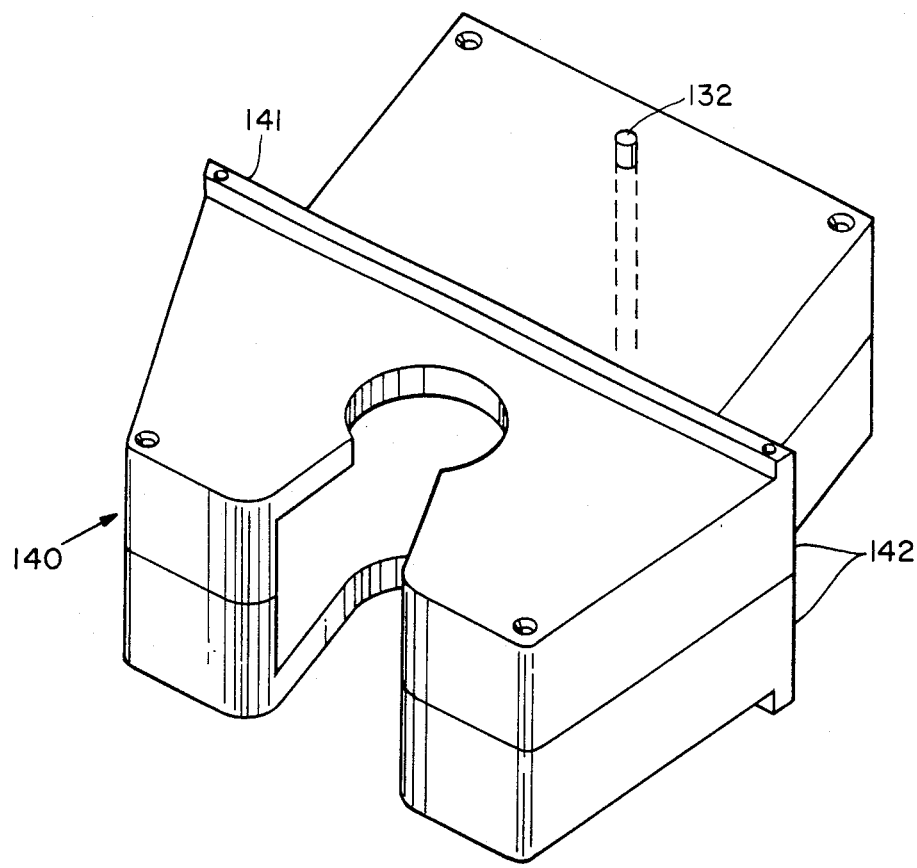
FIG. 11 illustrates in plan view the housing for the pressure of FIG. 9 that is mounted on the front panel in FIG. 4A.

FIGS. 9-11 illustrate the structure and calibration system for measuring the fluid pressure in a flexibly walled filter chamber through which the blood passes.

FIG. 11 shows the housing 140 for the sensor 130 which can be seen extending from the front panel of the unit in FIG. 4A. The housing 140 is divided into upper and lower halves 142 which separate to allow access to internal sensor apparatus. Panel 141 is used to mount the sensor onto the front panel 99 of the unit.

The pressure sensor 130 is comprised of two opposed arms 131A and 131B rotatable in a plane orthogonal to the longitudinal axis of axle 132. A spring 133 is mounted between posts 137 imbedded in arms 131 and operates to pull the two arms together. A magnet 135 is mounted in arm 131A directly below a Hall effect sensor 134 mounted on the second arm 131B by current carrying fingers 136 extending into the second arm. Sensor 134 detects any movement of the two arms 131A and 131B relative to each other due to the resulting change in the magnetic flux of magnet 135 around the sensor 134. The sensor 134 generates an electrical signal whose voltage varies with the change in distance between the two arms 131A and 131B.

FIG. 10 illustrates how the sensor 130 is calibrated. A hand pump 152 is used to pressurize the interior 154 of the disposable filtration chamber 151. The arms 131 of the sensor 130 engage opposite sides of the flexible wall of chamber 154. Pressure readings taken from a gauge or standard pressure transducer 153 are matched with electrical signals generated by Hall effect sensor 134 for each pressure level in the chamber. The expansion or contraction of the walls of chamber 154 due to the fluid pressure therein is be uniquely identified by the output of the pressure sensor 130 at any time. Thus a unique function is provided by correlating chamber pressure with the voltage of the signal generated by sensor 134.

Two guides 150 positioned above and below the sensor 134 are used to mount the chamber 151 on the front panel of the cabinet so that the arms 131 are properly aligned about chamber 154.

We claim:

1. Centrifuge apparatus for processing biological fluids comprising:

a cylindrical stationary bucket having a closeable top opening and a transverse inner diameter D1;

a centrifuge disposed within said bucket comprising:
- (a) a bowl rotatable about a longitudinal axis and having a seamless integral bowl body with a main body portion of generally cylindrical shape and transverse outer diameter D2 and a lower projecting portion of smaller diameter than D2;
- (b) a non-rotating head on said bowl providing a pathway for entry and exit of fluid from said bowl while the bowl is rotating;
- (c) a chuck for holding said bowl for rotation said chuck having a cylindrical upper portion of outer diameter D3 and inner diameter D4 conforming in shape to the shape of the main body portion and wherein D1 minus D3 is very small and D4 minus D2 is likewise very small;
- (d) a closeable cover over said bucket for holding the head of the bowl in a stationary position; and
- (e) motor means for rotating said chuck and bowl within said bucket about the longitudinal axis.

2. The apparatus of claim 1 wherein said motor means comprises a variable speed motor for driving said bowl and means for providing electrical power to said motor.

3. The apparatus of claim 2 further comprising a sensor for detecting whether the cover is closed such that power is provided to said motor only when the cover is closed.

4. The apparatus of claim 1 further comprising locking means for locking the cover in a closed position.

5. The apparatus of claim 4 further comprising a main processor and means for detecting whether said cover is locked and wherein said main processor is signaled by said detecting means and in response thereto said main processor enables the motor only when said locking means is locked.

6. A centrifuge for processing biological fluids comprising:

a cylindrical stationary housing having an inner cylindrical shape;

a chuck for frictionally holding a centrifuge bowl within the housing for rotation about a longitudinal axis of the bowl, said chuck having an outer wall closely conforming in shape along a major portion thereof to the cylindrical shape of said housing and which chuck is rotatable in spaced apart close proximity within said housing and an inner wall closely conforming in shape to a major portion of said bowl such that when said bowl is inserted in said chuck it nests within said inner wall;

a motor having a fixed stator and a hollow rotor for rotating said chuck and bowl about said longitudinal axis; and a longitudinally hollow shaft affixed at one end to said chuck and at an opposite end to said rotor, such that a continuous longitudinal transverse opening which during operation extends continuously unobstructed to the atmosphere from the chuck through the rotor for expulsion of air from the chuck when the bowl is inserted therein.

7. The centrifuge of claim 6 wherein the major portion of the chuck comprises a cylindrical walled member and an angularly inclined lower wall surface extends therefrom to a lower vertical wall and an end wall with an opening therein.

8. The centrifuge of claim 6 further comprising means for damping vibration of the housing.

9. The centrifuge of claim 8 wherein said damping means is comprised of a metal ring mass in the housing concentrically disposed around the chuck.

10. The centrifuge of claim 6 wherein said motor is a variable speed synchronous electric motor.

11. A centrifuge for processing biological fluids comprising:

a stationary hollow cylindrical shaped bucket; and a rotatable, generally cylindrically shaped, chuck disposed within said bucket, for holding a disposable plastic fluid processing bowl having a cylindrically shaped peripheral outer surface, and wherein said chuck is adapted for rotation about a longitudinal axis of said bowl, and wherein said chuck has an inner surface shape which for a substantial longitudinal length of said bowl, conforms to the shape of said bowl and the chuck has an outer shape which conforms to the shape of said bucket and fits within said bucket in closely spaced relationship thereto.

12. The centrifuge of claim 11 wherein the bowl has a bowl body which is comprised of a single blow molded piece having a smooth central longitudinal outer surface to which the inner surface of the chuck conforms.

13. The centrifuge of claim 11 wherein the bucket has an open top and wherein the outer diameter of the chuck is close to, but less than, the diameter of the opening in said top.

14. The centrifuge of claim 13 wherein the bowl is adapted to be inserted through said opening into said chuck and held for rotation therein by frictional engagement between an inner surface of the chuck and an external surface of the bowl.

15. The centrifuge of claim 14 wherein the frictional engagement between the chuck and the bowl is provided without the use of mechanical locking devices between the chuck and the bowl in the space between the peripheral outer surface of the bowl and the shaped surface of the chuck along the substantial longitudinal length thereof.

16. A centrifuge for processing biological fluids comprising:

a stationary bucket having an open top; and a rotatable, generally cylindrically shaped chuck disposed within said bucket and having an outer diameter close to, but less than, the diameter of the open top, wherein said chuck is adapted for holding a disposable plastic fluid processing bowl having a cylindrically shaped peripheral outer surface, and wherein said chuck is adapted for rotation about a longitudinal axis of said bowl, and wherein the inner shape of said chuck for a substantial longitudinal length of said bowl conforms to the shape of said bowl.

17. The centrifuge of claim 16 wherein the bowl has an upper ring portion, and upper diagonal portion extending radially inwardly from said ring portion, a middle central portion extending longitudinally from said upper diagonal portion, a lower diagonal portion extending radially inwardly from said middle central portion, and a bottom cross portion extending from said diagonal portion and the inner shape of the chuck conforms to the middle central portion of the bowl and the lower diagonal portion and the bottom cross portion except that a bore extends through the corresponding cross portion of said chuck.

18. A centrifuge for processing biological fluids comprising:

a housing;

a chuck for frictionally holding a centrifuge bowl within the housing for rotation about a longitudinal axis of the bowl, said chuck comprising a cylindrical walled member having an angularly inclined lower wall surface extending to a lower vertical wall and an end wall with an opening therein and with an internal circular groove in said vertical wall such that an O-ring positioned in said groove retains the bowl;

a motor having a fixed stator and a hollow rotor for rotating said chuck and bowl about said longitudinal axis; and a longitudinally hollow shaft affixed at one end to said chuck and at an opposite end to said rotor, such that a continuous longitudinal transverse opening extends from the chuck through the rotor for expulsion of air from the chuck when the bowl is inserted therein.

* * * * *